(12) United States Patent
Dietrich et al.

(10) Patent No.: US 11,166,651 B2
(45) Date of Patent: Nov. 9, 2021

(54) MEASURING ARRANGEMENT AND METHOD FOR IN-VIVO DETERMINATION OF THE LACTATE CONCENTRATION IN BLOOD BY MEANS OF ELECTROCHEMICAL IMPEDANCE SPECTROSCOPY

(71) Applicant: Kimal Sensors Ltd., Droitwich (GB)

(72) Inventors: Hendrik Dietrich, Aschaffenburg (DE); Raymond Glocker, Aschaffenburg (DE); Steve Minett, Uxbridge (GB); Alan Press, Uxbridge (GB)

(73) Assignee: KIMAL SENSORS LTD., Worcestershire (GB)

( * ) Notice: Subject to any disclaimer, the term of this patent is extended or adjusted under 35 U.S.C. 154(b) by 226 days.

(21) Appl. No.: 15/739,379

(22) PCT Filed: Jun. 23, 2016

(86) PCT No.: PCT/EP2016/001078
§ 371 (c)(1),
(2) Date: Dec. 22, 2017

(87) PCT Pub. No.: WO2016/206811
PCT Pub. Date: Dec. 29, 2016

(65) Prior Publication Data
US 2020/0315509 A1   Oct. 8, 2020

(30) Foreign Application Priority Data
Jun. 23, 2015   (DE) ..................... 10 2015 007 875.5

(51) Int. Cl.
*A61B 5/1455* (2006.01)
*A61B 5/145* (2006.01)
(Continued)

(52) U.S. Cl.
CPC ........ *A61B 5/14546* (2013.01); *A61B 5/0024* (2013.01); *A61B 5/02405* (2013.01);
(Continued)

(58) Field of Classification Search
None
See application file for complete search history.

(56) References Cited

U.S. PATENT DOCUMENTS 5,945,832 A   8/1999   Harvey, III et al.
6,361,501 B1   3/2002   Amano et al.
(Continued)

FOREIGN PATENT DOCUMENTS

DE   10015818   10/2001
DE   60115301   6/2006
(Continued)

OTHER PUBLICATIONS

International Search Report and Written Opinion received in corresponding PCT Application No. PCT/EP2016/001078, dated Sep. 29, 2016.

*Primary Examiner* — Eric F Winakur
*Assistant Examiner* — Marjan Fardanesh
(74) *Attorney, Agent, or Firm* — Grossman, Tucker, Perreault & Pfleger, PLLC (57) ABSTRACT

A measuring arrangement for in-vivo determination of the lactate concentration in blood by means of electrochemical impedance spectroscopy, comprising a substantially flat shaped probe having a longitudinal extension, a transverse extension and a thickness, wherein the longitudinal extension and the transverse extension of the probe are each a multiple of the thickness of the probe, an analyzer circuitry connected to the probe, and communication means connected to the analyzer circuitry for transferring data via a WPAN, wherein the substantially flat shaped probe is
(Continued)

arranged at an edge of the measuring arrangement, so that the probe, during operation of the measuring arrangement, faces the animal or human body to be examined, in such a manner that the probe is arranged with its longitudinal and transverse extensions approximately parallel to the surface of the body to be examined, a wristband therefor, and a method for the operation thereof.

21 Claims, 4 Drawing Sheets

(51) Int. Cl.
*A61B 5/00* (2006.01)
*A61B 5/024* (2006.01)
*A61B 5/053* (2021.01)
*A61B 5/1468* (2006.01)
*A61B 5/1495* (2006.01)

(52) U.S. Cl.
CPC ............ *A61B 5/053* (2013.01); *A61B 5/1455* (2013.01); *A61B 5/1468* (2013.01); *A61B 5/1495* (2013.01); *A61B 5/681* (2013.01); *A61B 5/742* (2013.01); *A61B 2560/0214* (2013.01); *A61B 2562/0219* (2013.01); *A61B 2562/0271* (2013.01); *A61B 2562/16* (2013.01)

(56) References Cited

U.S. PATENT DOCUMENTS

| | | | |
|---|---|---|---|
| 6,411,841 B2 | 6/2002 | Heikkilae | |
| 7,432,068 B2 | 10/2008 | Frey et al. | |
| 9,939,462 B2 | 4/2018 | Glocker | |
| 2003/0186263 A1 | 10/2003 | Frey et al. | |
| 2006/0142968 A1* | 6/2006 | Han | A61B 5/0205 702/120 |
| 2010/0004517 A1 | 1/2010 | Bryenton et al. | |
| 2014/0350883 A1 | 11/2014 | Carter et al. | |
| 2015/0015276 A1* | 1/2015 | Glocker | A61B 5/14546 324/649 |
| 2015/0061837 A1 | 3/2015 | Honore et al. | |
| 2015/0126834 A1 | 5/2015 | Wang et al. | |

FOREIGN PATENT DOCUMENTS

| | | |
|---|---|---|
| DE | 69833656 | 8/2006 |
| DE | 102013008243 | 11/2014 |
| EP | 0947160 | 6/1999 |
| EP | 1127543 | 8/2001 |
| EP | 1319943 | 6/2003 |
| EP | 2803316 | 11/2014 |
| GB | 2516259 | 1/2015 |
| JP | 11-133159 | 5/1999 |
| WO | 97/21094 | 6/1997 |

\* cited by examiner

MEASURING ARRANGEMENT AND METHOD FOR IN-VIVO DETERMINATION OF THE LACTATE CONCENTRATION IN BLOOD BY MEANS OF ELECTROCHEMICAL IMPEDANCE SPECTROSCOPY

FIELD

The invention relates to a measuring arrangement for in-vivo determination of the lactate concentration in blood by means of electrochemical impedance spectroscopy, and to a method for operating the measuring arrangement.

BACKGROUND

It is known to determine the concentration of hematocrit in the blood by means of electrochemical resonance spectroscopy. This is carried out with excitation at frequencies in the region of 100 kHz.

From DE 100 15 818 A1 there is known a biosensor and a method for determining macromolecular biopolymers, in which an impedance measurement is carried out at 50 mV by means of probe molecules immobilised on electrodes in order to determine DNA strands. A first and a second electrode are thereby to be subdivided into a plurality of electrode segments which are electrically insulated from one another, wherein randomly selected electrode segments can be electrically coupled independently of one another so that an effective electrode surface can be adjusted in size independently of the selected electrode segments.

From WO 97/21094 A1 there is known an impedance measuring system for identifying molecular structures in a sample solution. The described sensor comprises an insulating layer having a plurality of channels spaced apart from one another in substantially the same direction. A side wall of each channel and the upper side of the insulating substrate are metallised to form an electrode. The test solution is to be located inside and between the channels.

From U.S. Pat. No. 5,945,832 there is known an apparatus and a method for measuring electrical properties of an electrically conductive molecule. To that end, a first metal contact face is provided with an insulating layer and a second contact face is applied to the insulating layer, in such a manner that an edge forms at a molecular distance from the first contact face. A conductive organic molecule having a metal binding group is coupled with the metal contacts.

From EP 1 319 943 A2 there is known an impedance sensor for analytes in liquid solution. The sensor is said to have two in particular flat conductors spaced apart from one another. An analyte to be tested is introduced into a measuring chamber between the conductors, which changes the impedance of the sensor.

In principle, it is known that frequency-dependent measurements in the range of from a few kHz to approximately 100 GHz give information about dynamic processes at molecular level.

From DE 10 2013 008 243 A1, EP 2 803 316 A1 and US 2015/0015276 A1 there is known a probe for measuring biomolecules by means of electrochemical impedance spectroscopy, which probe can be inserted invasively into a blood vessel by means of a catheter for in-vivo measurement. To that end, the probe has a long length in comparison to its thickness and width. By means of a special configuration of the conductor structure at the distal end of the probe, radiation characteristics of the probe that are adapted to the extremely near field examination are achieved.

The described probe has the disadvantage that it must be inserted invasively into the human or animal body to be examined. Such a probe is therefore suitable primarily for use in monitoring patients in the field of hospital care. Accordingly, it is described as being particularly advantageous that such a probe can be used in the side lumen of multi-lumen catheters, as are frequently used in the care of intensive care patients, for early detection of the onset of sepsis.

However, changes in the lactate level are also an indicator of further pathological changes as well as of physiological changes due to stress. From EP 1 127 543 A1 and DE 601 15 301 T2 it is known to determine a training programme that is individually matched to the physical capacity and the current state of health of an athlete by continuously assessing the lactate concentration in the body. To that end, the measured data of a heart monitor worn by or connected to the athlete during training are used and, with the aid of numerous data and a neuronal network, an assessment of the lactate concentration in the body is carried out non-invasively via a mathematical model which models the lactate concentration in the body. Similar attempts at objectivising the training load of an athlete by using diagnostic methods from Asiatic medicine are known from EP 0 947 160 A1 and DE 698 33 656 T2. To that end, using a pulse wave diagnosing device which is worn like a wristwatch, the pulse waveform is detected, analysed and linked with numerous other physiological data of the athlete. By means of frequency analysis and filtering of the data, a correlation with physiological states of the athlete known in traditional Far Eastern medicine is made.

SUMMARY

Accordingly, the object of the invention is to provide a measuring arrangement which opens up further fields of use for the determination of the lactate concentration.

The object is achieved according to the invention by a measuring arrangement for in-vivo determination of the lactate concentration in blood by means of electrochemical impedance spectroscopy, comprising a substantially flat shaped probe having a longitudinal extension, a transverse extension and a thickness, wherein the longitudinal extension and the transverse extension of the probe are each a multiple of the thickness of the probe, an analyzer circuitry connected to the probe, and communication means connected to the analyzer circuitry for transferring data via a WPAN, wherein the substantially flat shaped probe is arranged at an edge of the measuring arrangement, so that the probe, during operation of the measuring arrangement, faces the human or animal body to be examined, in such a manner that the probe is arranged with its longitudinal and transverse extensions approximately parallel to the surface of the body to be examined. The object is further achieved by a method for operating such a measuring arrangement.

The measuring arrangement can be fixed to the body of a body to be examined by means of a medical adhesive tape, for example. Particularly good measuring results can be achieved if the measuring arrangement is attached in the region of an artery or of a tissue which otherwise has a good blood supply.

It is particularly advantageous, as well as simple and convenient for a user, to use the measuring arrangement according to the invention with a wristband having a receptacle for a measuring arrangement, characterized in that the receptacle is so arranged that the probe of the measuring arrangement, when the wristband is used as intended, is situated in use in the region of the radial artery of a human arm, and in that the receptacle preferably has a viewing window for viewing a display of the measuring arrangement.

In the leisure sector, the invention can be used particularly well for prevention with a set of one or more wristbands and a measuring arrangement, if the measuring arrangement is inserted removably into the receptacle of the wristband, so that one measuring arrangement can be used with a plurality of wristbands. It is thereby possible to take fashion aspects into consideration and, for example, to use a measuring arrangement having a colour that matches clothing. In the medical sector, it is possible in a simple manner to identify patients of particular groups or having particular requirements by allocating a wristband on the basis of colour, or to replace the wristband for hygiene reasons after it has been used by a patient.

The object is further achieved by a method for operating a measuring arrangement according to the invention, wherein the probe is activated intermittently by the analyzer circuitry, wherein, in a first operating mode, the probe is excited in the frequency range around 100 MHz for determination of the lactate concentration by means of electrochemical impedance spectroscopy, and preferably, in a second operating mode, the probe is excited in the frequency range around 5 kHz for determination of the heart rate by means of electrochemical impedance spectroscopy.

BRIEF DESCRIPTION OF THE DRAWINGS

The invention will be described in greater detail below by means of an exemplary embodiment shown in the accompanying drawings, in which.

DETAILED DESCRIPTION

Figure 1:
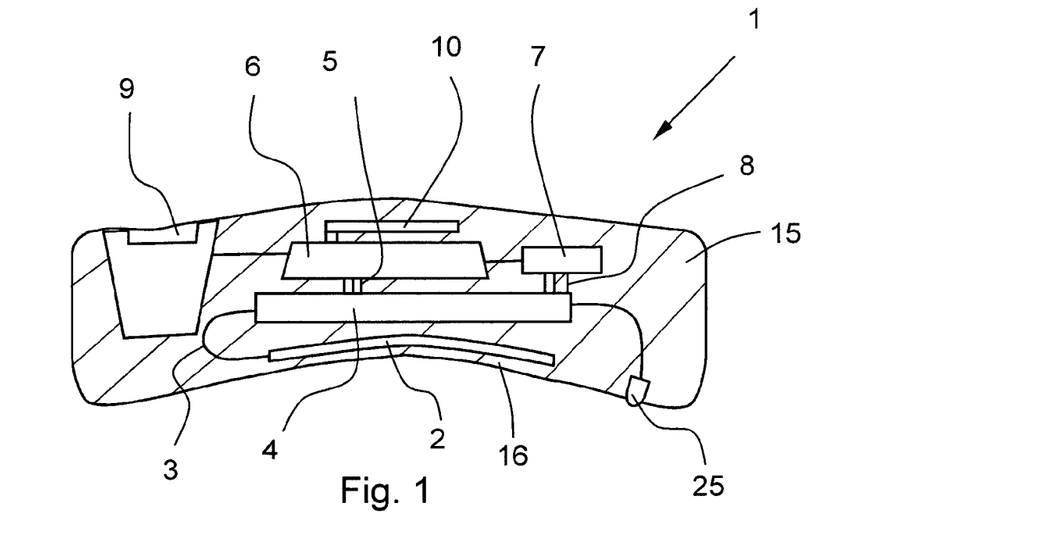
FIG. 1 shows a cross-section of a measuring arrangement according to the invention.

FIG. 1 shows a cross-section of a measuring arrangement according to the invention for in-vivo determination of the lactate concentration in blood by means of electrochemical impedance spectroscopy, designated as a whole by 1. The measuring arrangement 1 comprises a substantially flat shaped probe 2, which is shown in greater detail in FIGS. 2 and 3. The measuring arrangement 1 further comprises an analyzer circuitry 4 connected to the probe 2 via a HF line 3. The analyzer circuitry 4 is further connected via an electric line 5 to a communication means 6.

In the preferred embodiment of the invention shown there is further provided an energy supply means 7 having an accumulator for electrical energy in the form of a battery, and a means for contactless charging of the accumulator 7. The battery 7 is connected to the analyzer circuitry 4 and to the communication means 6 via supply lines 8. Furthermore, a display 9 with corresponding actuation circuitry is also provided. Operating parameters, such as the charge state of the battery 7, or information or measured values which are intended for the user can be displayed via the display 9.

Finally, an antenna 10 is also provided, which antenna is connected to the communication means 6. The antenna 10 serves to transfer the data from the communication means 6 via a WPAN. There is suitable as the WPAN (wireless personal area network), for example, a connection via Bluetooth 4.0 standard. The use of the BLE protocol (Bluetooth low energy) permits particularly low energy consumption. Alternatively or in addition, other near field communication (NFC) antennae and protocols can be provided.

The probe 2, as well as also the analyzer circuitry 4, the communication means 6, the energy supply means 7, the display 9, the antenna 10 and the lines 3, 5, 8, are embedded into a housing 15. The housing is made of a non-polar material, preferably a polyurethane elastomer (UR) or a silicone rubber (silicone SR).

Figure 2:
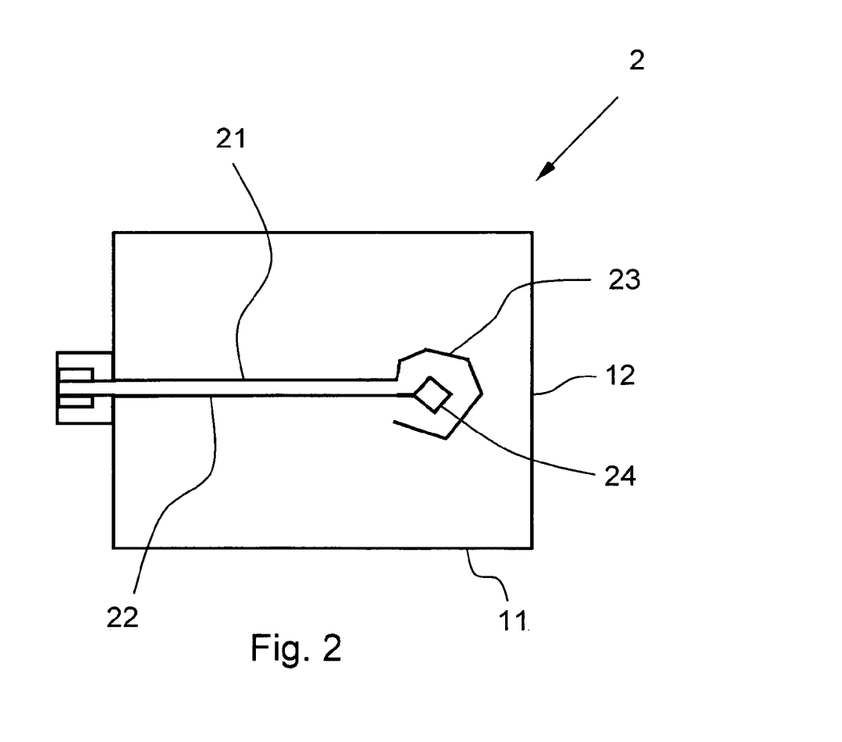
FIG. 2 shows a top view of a probe of a measuring arrangement according to the invention.
Figure 3:
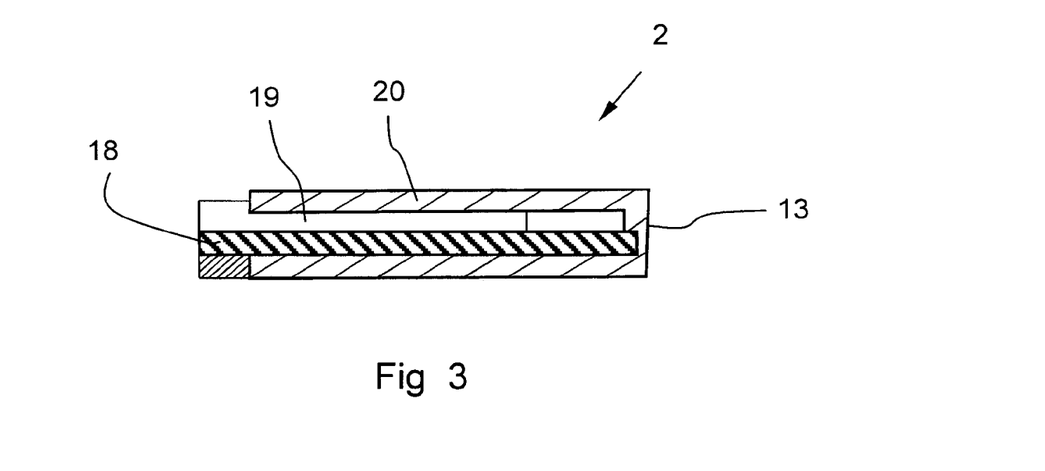
FIG. 3 shows the probe of FIG. 2 in cross-section.

The probe 2, which is shown in greater detail in FIGS. 2 and 3, has a longitudinal extension 11, a transverse extension 12 and a thickness 13. The longitudinal and transverse extensions 11, 12 of the probe 2 are each a multiple greater than the thickness 13 of the probe 2. The probe 2 is accordingly substantially flat shaped. The probe 2 is arranged at an edge of the measuring arrangement 1, so that the probe 2, during operation of the measuring arrangement, faces the human or animal body 14 to be examined, in such a manner that the probe 2 is arranged with its longitudinal and transverse extensions 11, 12 approximately parallel to the surface of the body 14 to be examined, see in particular FIGS. 1, 4 and 5.

The housing 15 has a sensor side which, during use of the measuring arrangement 1, faces the human or animal body 14 to be examined, in particular is adjacent to the skin. The probe 2 with its longitudinal and transverse extensions 11, 12 is immediately adjacent to the sensor side in the housing 2, the sensor side of the housing 2 being in the form of a membrane 16 covering the probe.

FIG. 3 shows that the probe 2 advantageously has the following configuration along a cross-section of its thickness 13: a base layer 18 of an insulating material, at least one layer of a conducting material 19 on a first side of the base layer 18, wherein the conducting material 19 covers only a portion of the surface of the base layer 18, as can be seen in FIG. 2. The side of the at least one layer of conducting material 19 opposite the base layer 18 is covered externally with an outer layer 20 of an insulating material. The at least one layer of a conducting material 19 is shaped into a conductor structure on the first side of the base layer 18, as can be seen in FIG. 2. The conductor structure comprises at least two conductors 21, 22 galvanically separated from each other, wherein each of the two conductors 21, 22 is connected to the HF line 3. At least one of the conductors 21, 22 is of substantially elongated shape and forms, over a portion of its longitudinal extension, an open annular portion 23 which is at an angle with respect to the remainder of the conductor 21, wherein the open annular portion 23 is preferably in the form of a polygon having from two to ten corners, further preferably from five to nine corners, particularly preferably six, seven or eight corners. The other conductor 22 is likewise of substantially elongated shape and terminates in an annular or filled enlarged portion 24, which is arranged concentrically inside the annular portion 23.

The measuring arrangement 1 further has preferably at least one temperature sensor 25, wherein the at least one temperature sensor 25 is arranged directly or by way of a metallic conductive heat transfer element on the exterior of the sensor side of the housing 15. The temperature sensor 25 is connected to an evaluation circuitry, which is here integrated into the analyzer circuitry 4, for outputting a digital value corresponding to the measured temperature. The temperature sensor 25 is advantageously in the form of an NTC. The body temperature fluctuates during the day a and also in dependence on mental and physical stress. The data from the temperature measurement can therefore be included in the evaluation of the remaining measured values.

The measuring arrangement 1 can be fixed to the body of a body to be examined by means of a medical adhesive tape, for example. Particularly good measurement results can be achieved if the measuring arrangement is attached in the region of an artery or of a tissue which otherwise has a good blood supply. Attachment in that manner is particularly expedient in the field of medical diagnosis and treatment, whether it be for long-term treatment or within the context of nursing.

Figure 4:
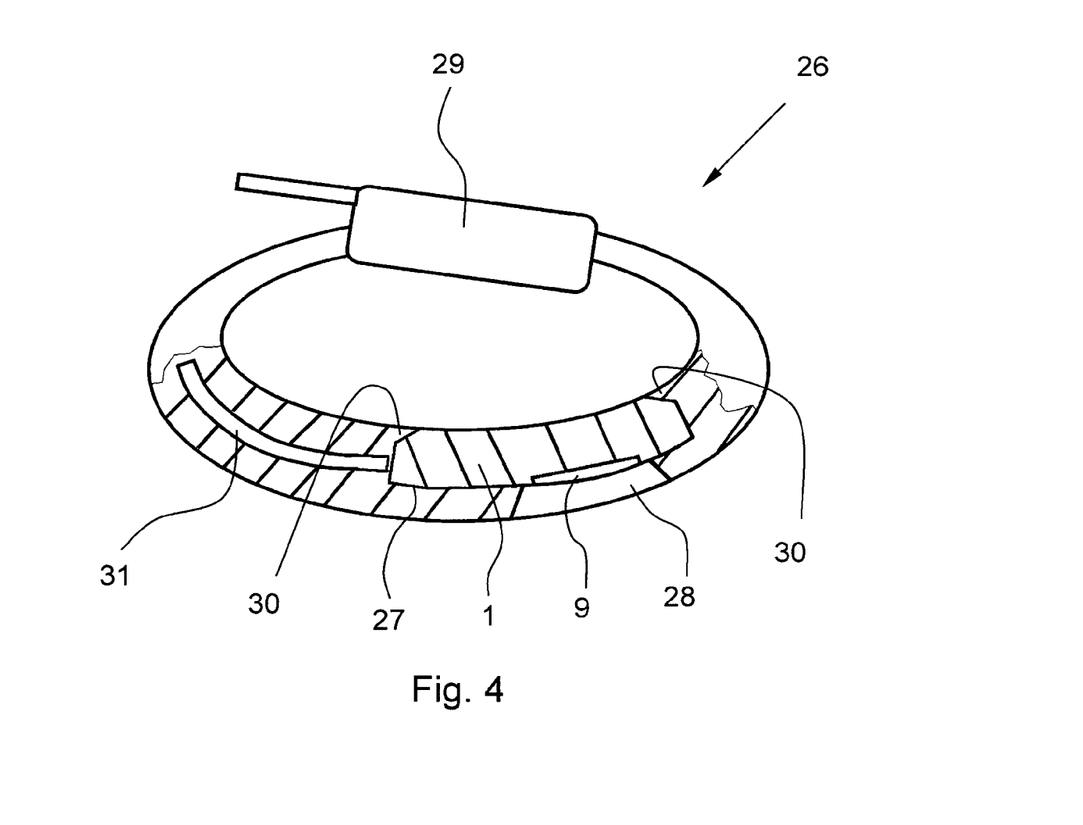
FIG. 4 shows a wristband according to the invention with a measuring arrangement according to the invention.
Figure 5:
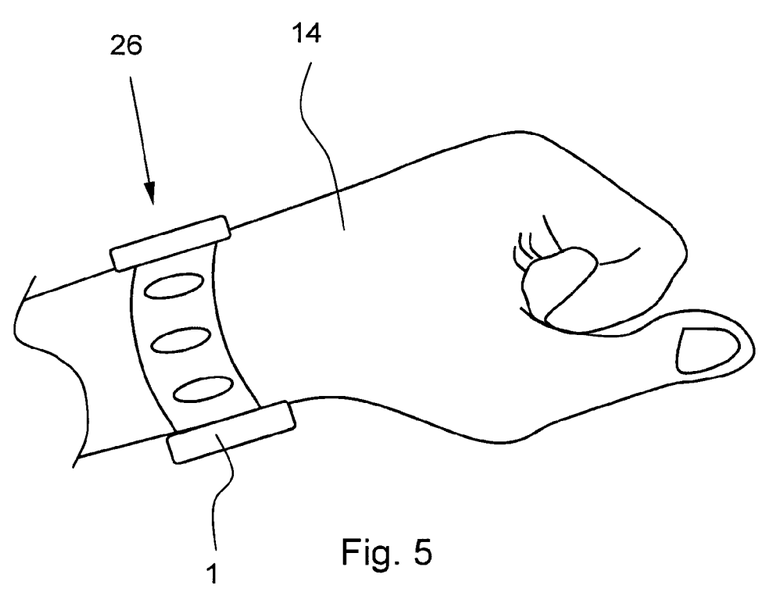
FIG. 5 shows a wristband according to the invention with a measuring arrangement according to the invention on the arm of a user.

It is particularly advantageous, as well as simple and convenient for a user, to use the measuring arrangement 1 according to the invention with a wristband 26 having a receptacle 27 for a measuring arrangement 1, as can be seen in partial section in FIG. 4. The receptacle 27 is so arranged that the probe 2 of the measuring arrangement 1, when the wristband 26 is used as intended, is situated in use in the region of the radial artery of a human arm 14, and that the receptacle preferably has a viewing window 28 for viewing a display 9 of the measuring arrangement 1.

In the leisure sector, the invention can be used particularly well for prevention with a set of one or more wristbands 26 and a measuring arrangement 1, if the measuring arrangement 1 is inserted removably into the receptacle 27 in the wristband 26, so that one measuring arrangement 1 can be used with a plurality of wristbands 26. It is thereby possible to take fashion aspects into consideration and, for example, to use a measuring arrangement 1 having a colour that matches clothing. In the medical sector, it is possible in a simple manner to identify patients of particular groups or having particular requirements by allocating a wristband 26 on the basis of colour, or to replace the wristband 26 for hygiene reasons after it has been used by a patient.

The wristband 26 comprises a locking means 29 for adjusting the size and/or for closing the wristband 26. The receptacle 27 for the measuring arrangement 1 is so designed that the measuring arrangement 1 can be removed only when the locking means 29 is open. As is shown in FIG. 4, this can be achieved, for example, in that the receptacle 27 faces inwards so that the measuring arrangement 1 can be inserted or removed only when the wristband 26 is not on an arm 14. Furthermore, resilient holding lugs or ribs 30 can be provided which hold the measuring arrangement 1 in position even when the locking means 29 of the wristband 26 is open. For removing the measuring arrangement 1 from the wristband 26, it is expedient for the viewing window 28 to be of sufficiently large dimensions that the measuring arrangement 1 can easily be pushed out of the receptacle 27 from the outside using a finger.

For a low energy consumption of the communication means 6 or for increasing the range in the case of WPAN communication, it is expedient for the wristband 26 to have an integrated WPAN antenna 31 for contactless coupling to the communication means 6 of the measuring arrangement 1.

The wristband is advantageously made substantially, for example apart from the WPAN antenna 31, of a non-polar material, preferably a polyurethane elastomer or a silicone rubber as described above, and/or the wristband 26 is integral with the housing 15 of the measuring arrangement 1.

Figure 6:
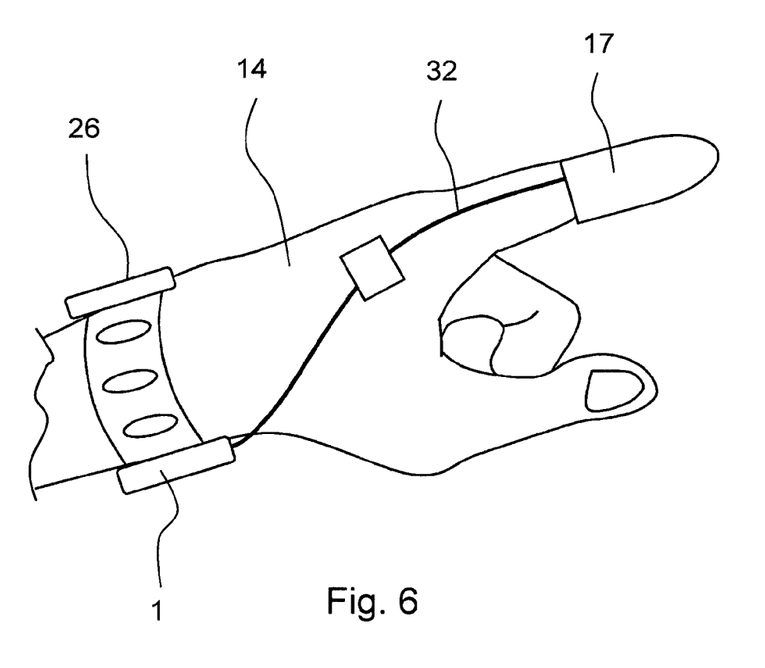
FIG. 6 shows a wristband according to the invention with a measuring arrangement according to the invention on the arm of a user, with a pulse oximeter.

As is shown in FIG. 6, the measuring arrangement 1 has an interface for connecting a pulse oximeter 17 and is connected to a circuitry for converting the signals from the pulse oximeter 17 into a digital value, which circuitry is here integrated into the analyzer circuitry 4 and is thereby connected to the communication means 6 for transferring the values via a WPAN. The pulse oximeter 17 is connected to the measuring arrangement 1 by a connecting line 32; however, the connection can also be effected wirelessly via an NFC (wireless interface for near field communication).

The measuring arrangement 1 has a unique individual identifier, which is also transmitted by the communication means 6 during data transfer and allows unequivocal assignment of the data to the measuring arrangement 1. The measuring arrangement 1 is assigned to the patient once, and in the case of further measurements the measured data are in each case assigned automatically to the correct patient without the nursing staff having to be concerned therewith. With an appropriate hospital infrastructure, fully automatic online monitoring of the patient is possible.

The probe 1 is activated intermittently by the analyzer circuitry, wherein, in a first operating mode, the probe is excited in the frequency range around 100 MHz, for example by wobbling between 70 MHz and 165 MHz, for determination of the lactate concentration by means of electrochemical impedance spectroscopy, and preferably, in a second operating mode, the probe is excited in the frequency range around 5 kHz for determination of the heart rate by means of electrochemical impedance spectroscopy.

For a particularly low energy consumption of a measuring arrangement 1 according to the invention, the probe is activated intermittently by the analyzer circuitry, wherein, in standard operating mode, the excitation of the probe in the frequency range around 100 MHz for determination of the lactate concentration by means of electrochemical impedance spectroscopy is performed once per time period, and in monitoring operating mode, the excitation is performed from two to eight times per time period, wherein the time period is between approximately 20 minutes and approximately 30 minutes, wherein excitation in monitoring operating mode is preferably performed every 5 to 10 minutes.

Excitation of the probe 2 in the frequency range around 100 MHz for determination of the lactate concentration by means of electrochemical impedance spectroscopy and in the frequency range around 5 kHz for determination of the heart rate by means of electrochemical impedance spectroscopy take place at different times, preferably the excitation in the frequency range around 5 kHz for determination of the heart frequency by means of electrochemical impedance spectroscopy is performed chronologically between two excitations for determination of the lactate concentration.

Advantageously, each of the temperature sensors 25 is actuated intermittently by the evaluation circuitry 4 for detecting the surface temperature of the sensor area of the housing 15, wherein the detection of the temperature preferably takes place at the same time intervals as the determination of the lactate concentration by means of electrochemical impedance spectroscopy, wherein, further preferably, the detection of the temperature is performed at a time when neither the excitation of the probe for determination of the lactate concentration nor the excitation for determination of the heart frequency is taking place.

The measured data and the unique individual identifier are sent by the communication means via a WPAN connection directly or via a telecommunication device and a gateway to a central data processing means, where they are evaluated, stored and further processed, and the values generated from the evaluation or information for the user are optionally transmitted to the measuring arrangement for outputting to a user.

The evaluated data are linked to base data assigned to a user via the unique individual identifier for calibration purposes, and also linked to data obtained from other sources, particularly lactate concentrations from laboratory testing, and the measuring arrangement is periodically recalibrated, preferably after approximately 8 hours, by comparison with current stored data, and the calibration data are transmitted to the measuring arrangement.

An intermediate memory is advantageously provided in the analyzer circuitry 4 for offline measurement.

Figure 7:
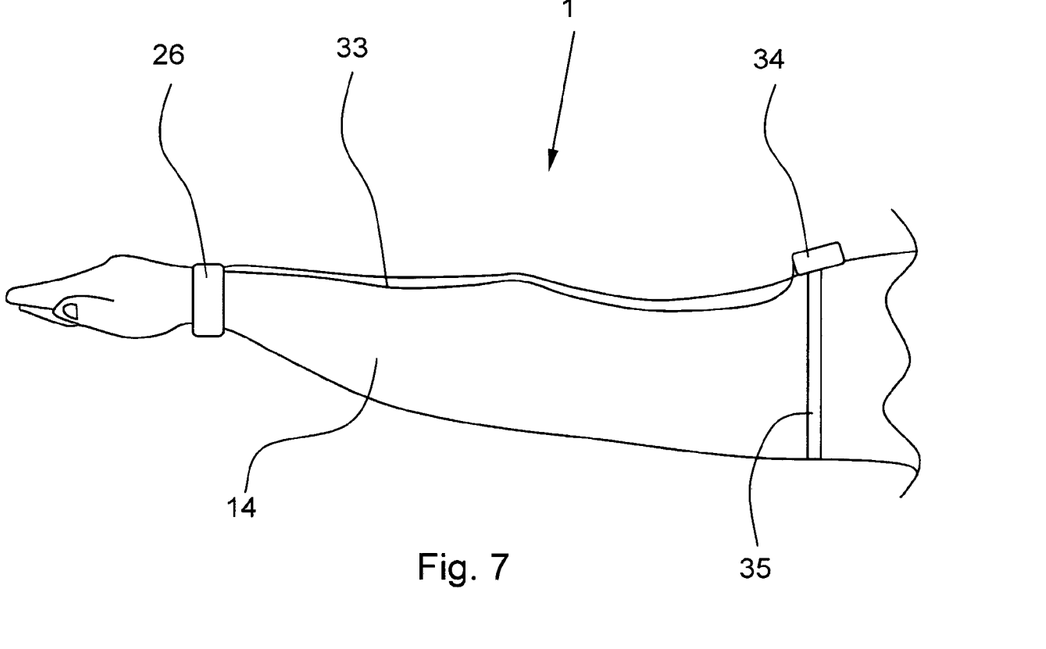
FIG. 7 shows of a measuring arrangement according to the invention comprising a wristband and an upper arm cabinet.

FIG. 7 shows an alternative embodiment of a measuring arrangement according to the invention comprising a wristband 26 and an upper arm cabinet 34. The cabinet 34 is connected to the wristband 26 and the probe 2 and temperature sensor 25 therein by way of connecting cable 33, which transmits the RF signals and sensor signals as well as comprising a power supply line. The cabinet 34 is arranged to be fixed to the upper arm of the body 14 of a person to be monitored by strap 35. This alternative arrangement allows to use more powerful analyzer circuitry 4' and to provide a larger battery 7' for power supply of the measuring arrangement 1. This allows to include for instance also the detection of blood alcohol concentration, thus providing for additional safety applications, like for long distance bus drivers or drivers of hazardous goods carrying lorries.

Figure 8:
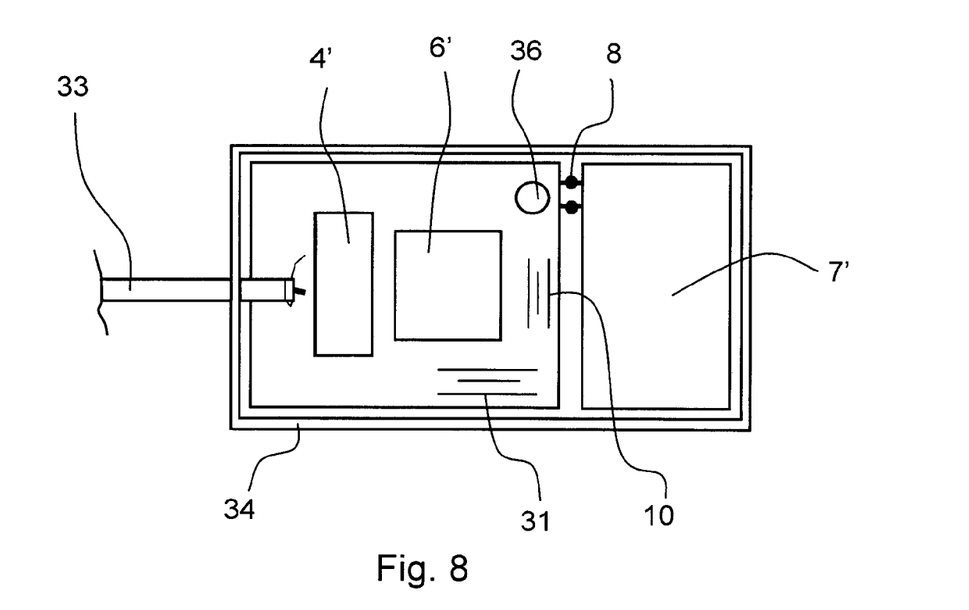
FIG. 8 shows a schematic view into the cabinet of FIG. 7 with cover removed.

FIG. 8 shows a schematic view into the cabinet 34 of the arrangement shown in FIG. 7 with cover removed. Besides the components mentioned with respect to the embodiments described above, like communication means 6', antenna 10 and WPAN antenna 31, an acceleration sensor 36 is provided for determining the acceleration of the cabinet 34 and the upper arm of body 14. The analysis of the acceleration figures compared to prestored value patterns allows to identify the person wearing the measuring arrangement 1 becoming tired, thus allowing alarm systems to be activated for preventing accidents.

What is claimed is:

1. A measuring arrangement for in-vivo determination of lactate concentration in blood by electrochemical impedance spectroscopy, comprising:
   a housing,
   a substantially flat shaped probe having a longitudinal extension, a transverse extension and a thickness, wherein the longitudinal extension and the transverse extension of the probe are each a multiple of the thickness of the probe,
   analyzer circuitry connected to the probe, and
   communication means connected to the analyzer circuitry to transfer data via a wireless personal area network (WPAN),
   wherein the substantially flat shaped probe, the analyzer circuitry and the communication means are arranged in the housing,
   wherein the substantially flat shaped probe is arranged at an edge of the housing, such that the probe, during operation of the measuring arrangement, faces an animal body or a human body to be examined, such that the probe is arranged with the longitudinal and transverse extensions approximately parallel to a surface of the body to be examined.

2. The measuring arrangement according to claim 1, wherein the probe is embedded into the housing, and the housing is made of a non-polar material, and
   wherein the non-polar material is at least one of an elastomer or a rubber.

3. The measuring arrangement according to claim 2, wherein the housing has a sensor side which, during the operation of the measuring arrangement, faces the animal body or the human body to be examined, and
   wherein the probe is arranged in the housing with the longitudinal and transverse extensions adjacent to the sensor side.

4. The measuring arrangement according to claim 3, wherein the measuring arrangement further comprises at least one temperature sensor arranged in the housing,
   wherein the at least one temperature sensor is arranged directly or by way of a metallic conductive heat transfer element on an exterior of the sensor side of the housing, and
   wherein the at least one temperature sensor is connected to an evaluation circuitry to output a digital value corresponding to a measured temperature, and
   wherein the evaluation circuitry is integrated with the analyzer circuitry.

5. The measuring arrangement according to claim 2, wherein at least one of the analyzer circuitry, the communication means, and an energy supply are embedded into the housing, and further comprising a display arranged in the housing.

6. The measuring arrangement according to claim 5, wherein the energy supply comprises an accumulator for electrical energy and is configured to contactlessly charge the accumulator.

7. The measuring arrangement according to claim 2, wherein the housing comprises a wristband.

8. The measuring arrangement according to claim 1, wherein the measuring arrangement further comprises an interface to connect a pulse oximeter, and the interface is connected to a circuitry to convert signals from the pulse oximeter into a digital value, and
   wherein the circuitry to convert signals from the pulse oximeter into a digital value is integrated with the analyzer circuitry.

9. The measuring arrangement according to claim 1, wherein the probe has a configuration along a cross-section of the thickness comprising:
   a base layer of an insulating material,
   at least one layer of conducting material on a first side of the base layer,
   wherein the at least one layer of conducting material covers only a portion of a surface of the base layer,
   wherein a side of the at least one layer of conducting material opposite the base layer has an external outer layer of an insulating material, and
   wherein the at least one layer of conducting material on the first side of the base layer is shaped into a conductor structure.

10. The measuring arrangement according to claim 9, wherein the conductor structure comprises at least two conductors galvanically separated from one another,
    wherein each of the at least two conductors is connected to a feeding line, wherein at least one of the at least two conductors is elongated and forms, over a portion of a longitudinal extension, an open annular portion which is at an angle with respect to a remainder of the conductor, and wherein the open annular portion is in a form of a polygon having from two to ten corners.

11. An article comprising the measuring arrangement according to claim 1 and further comprising at least one wristband having a receptacle, wherein the measuring arrangement is disposable in the at least one wristband, and is insertable into and removable from the receptacle of the at least one wristband.

12. The article according to claim 11, wherein the at least one wristband further comprises a lock to adjust size and/or close the wristband, and the measuring arrangement is removable from the receptacle of the at least one wristband only when the lock of the wristband to adjust size and/or close the wristband is open.

13. The article according to claim 11, wherein the communication means is operable with a WPAN antenna integrated in the wristband.

14. The measuring arrangement according to claim 1, wherein the measuring arrangement further comprises cabinet remote from the housing and a connecting cable to connect therebetween.

15. The measuring arrangement according to claim 1, further comprising an acceleration sensor.

16. A method for operating a measuring arrangement, comprising:
obtaining the measuring arrangement, the measuring arrangement comprising
a housing,
a substantially flat shaped probe having a longitudinal extension, a transverse extension and a thickness, wherein the longitudinal extension and the transverse extension of the probe are each a multiple of the thickness of the probe,
analyzer circuitry connected to the probe, and
communication means connected to the analyzer circuitry to transfer data via a wireless personal area network (WPAN),
wherein the substantially flat shaped probe, the analyzer circuitry and the communication means are arranged in the housing,
wherein the substantially flat shaped probe is arranged at an edge of the housing, such that the probe, during operation of the measuring arrangement, faces an animal body or a human body to be examined, such that the probe is arranged with the longitudinal and transverse extensions approximately parallel to a surface of the body to be examined,
arranging the probe facing the animal body or the human body with the longitudinal and the transverse extensions approximately parallel to the surface of the body,
activating the probe intermittently by the analyzer circuitry, wherein excitation of the probe is in a frequency range around 100 MHz, to determine lactate concentration in the animal body or the human body by electrical impedance spectroscopy, and
determining the lactate concentration in the animal body or the human body by the electrical impedance spectroscopy.

17. The method for operating the measuring arrangement, according to claim 16, wherein the activating of the probe intermittently by the analyzer circuitry, wherein excitation of the probe is in the frequency range around 100 MHz, is performed in either of
a standard operating mode wherein excitation of the probe is performed 1 time per time period, or
a monitoring operating mode wherein excitation of the probe is performed from 2 to 8 times per time period, and
wherein the time period is between approximately 20 minutes and approximately 30 minutes.

18. The method for operating the measuring arrangement, according to claim 16, further comprising:
activating the probe intermittently by the analyzer circuitry, wherein excitation of the probe is in a frequency range around 5 kHz, to determine heart rate in the animal body or the human body by electrical impedance spectroscopy, and
determining the heart rate in the animal body or the human body by the electrical impedance spectroscopy, and
wherein the activating of the probe intermittently by the analyzer circuitry, wherein the excitation of the probe is in the frequency range around 5 kHz, to determine heart rate in the animal body or the human body by electrical impedance spectroscopy is performed chronologically between a first and a second activating of the probe intermittently by the analyzer circuitry, wherein excitation of the probe is in a frequency range around 100 MHz, to determine lactate concentration in the animal body or the human body by electrical impedance spectroscopy.

19. The method for operating the measuring arrangement, according to claim 16, further comprising:
wherein the measuring arrangement further comprises at least one temperature sensor,
activating the at least one temperature sensor intermittently by the analyzer circuitry to detect a surface temperature of a sensor area of the housing, and
detecting the surface temperature of the sensor area of the housing.

20. The method for operating the measuring arrangement, according to claim 16, further comprising:
transferring data to determine lactate concentration in the animal body or the human body by electrical impedance spectroscopy to with the communication means, via a wireless personal area network (WPAN), and
evaluating the transferred data to determine lactate concentration in the animal body or the human body by electrical impedance spectroscopy.

21. The method for operating the measuring arrangement, according to claim 20, further comprising:
linking the evaluated data to stored data,
comparing the evaluated data with the stored data,
generating calibration data from the comparison of the evaluated data with the stored data,
transmitting the calibration data to the measurement arrangement, and
recalibrating the measurement arrangement from the calibration data.

* * * * *